United States Patent
Evans

(10) Patent No.: US 7,127,295 B2
(45) Date of Patent: Oct. 24, 2006

(54) DEVICE AND METHOD FOR PLACEMENT OF ELECTRODES IN THE GI TRACT

(76) Inventor: John R. Evans, 212 Summit Ave., Redlands, CA (US) 92373

( * ) Notice: Subject to any disclaimer, the term of this patent is extended or adjusted under 35 U.S.C. 154(b) by 29 days.

(21) Appl. No.: 11/119,097

(22) Filed: May 2, 2005

(65) Prior Publication Data
US 2005/0251219 A1    Nov. 10, 2005

Related U.S. Application Data

(60) Provisional application No. 60/567,776, filed on May 5, 2004.

(51) Int. Cl.
*A61N 1/18* (2006.01)
*A61N 1/05* (2006.01)
(52) U.S. Cl. ............... 607/40; 607/41; 607/133
(58) Field of Classification Search .......... 607/40, 607/41, 127, 128, 133; 600/375, 377, 380, 600/585, 593; 604/65–67, 503, 504, 505, 604/114, 118
See application file for complete search history.

(56) References Cited

U.S. PATENT DOCUMENTS

| | | |
|---|---|---|
| 3,411,507 A | 11/1968 | Wingrove |
| 5,007,900 A | 4/1991 | Picha et al. |
| 5,047,026 A | 9/1991 | Rydell |
| 5,292,344 A | 3/1994 | Douglas |
| 5,690,691 A | 11/1997 | Chen et al. |
| 6,254,598 B1 | 7/2001 | Edwards et al. |
| 6,258,087 B1 | 7/2001 | Edwards et al. |
| 6,363,937 B1 | 4/2002 | Hovda et al. |
| 6,535,764 B1 | 3/2003 | Imran et al. |
| 6,542,776 B1 | 4/2003 | Gordon et al. |
| 6,778,861 B1 * | 8/2004 | Liebrecht et al. ............ 607/116 |
| 2002/0072738 A1 | 6/2002 | Edwards et al. |
| 2002/0103424 A1 | 8/2002 | Swoyer et al. |
| 2002/0165589 A1 * | 11/2002 | Imran et al. ................. 607/40 |
| 2003/0167024 A1 | 9/2003 | Imran et al. |
| 2004/0024427 A1 | 2/2004 | Imran et al. |

FOREIGN PATENT DOCUMENTS

| | | |
|---|---|---|
| EP | 0 129 483 A1 | 12/1984 |
| EP | 0 571 938 A2 | 12/1993 |
| WO | WO 02/089655 A2 | 11/2002 |

* cited by examiner

*Primary Examiner*—Robert E. Pezzuto
*Assistant Examiner*—Tammie K. Heller
(74) *Attorney, Agent, or Firm*—Richard C. Litman

(57) ABSTRACT

The device and method for placement of an instrument, specifically electrodes, in the GI tract allows for placement of electrodes for gastric electrical stimulation into the gastric wall using endoscopic techniques. The device has one or more electrodes disposed on an elongated body having a pointed first end and a bolster disposed on a second end. When placed within the GI tract, the first end of the device extends through the gastric and abdominal walls, extending outside of the patient's body with the bolster in contact against the inner lining of the gastric wall to retain the device. Exposed electrodes contact the gastric smooth muscle. Insulated wires in electrical connection with the electrodes run the length of the device body. Once the device is placed, the first end of the device body is removed to expose the wires, allowing electrical connection to an external electrical signal generator to provide electrical stimulus.

20 Claims, 5 Drawing Sheets

DEVICE AND METHOD FOR PLACEMENT OF ELECTRODES IN THE GI TRACT

CROSS-REFERENCE TO RELATED APPLICATION

This application claims the benefit of U.S. Provisional Patent Application Ser. No. 60/567,776, filed May 5, 2004.

BACKGROUND OF THE INVENTION

1. Field of the Invention

The present invention relates to electrical stimulation of neuromuscular activity in the gastrointestinal (GI) tract by artificial gastric pacemakers. More specifically, the invention is a device and method for the placement of electrodes in the GI tract.

2. Description of the Related Art

Electrical impulses can be used to stimulate contractions in the gastrointestinal (GI) tract, much as an artificial pacemaker can stimulate contractions in the heart. Gastric electrical stimulation (GES) can be used in the treatment of gastroparesis, a disorder in which food moves through the stomach more slowly than normal, among other GI disorders. Electrical impulses can also be used to decrease appetite. The precise effect of GES appears dependent on the location of electrodes used to provide electrical stimulus, as well as the amplitude and frequency of the applied electrical impulse.

U.S. Pat. No. 3,411,507, issued on Nov. 19, 1965 to R. Wingrove, discloses a method of gastrointestinal stimulation with electrical pulses, for the management of the condition often referred to as paralytic ileus. The method involves nasogastrically placing a first electrode into a patient's stomach in proximity to or past the pyloric valve. A second electrode is applied to the patient's body at a convenient location such as the abdominal wall, and electrical impulses are applied between the electrodes. The result of the impulses is the inducement of peristaltic waves, and the restoration of peristaltic activity.

U.S. Pat. No. 5,292,344, issued on Mar. 8, 1994 to D. Douglas, discloses a percutaneously placed electrical gastrointestinal pacemaker stimulatory system including, as part of the system, a tubular device having one or more electrodes protruding from an end bolster. The device extends through the skin with the end bolster held in position against the inner lining of the gastrointestinal tract. Electrodes extending from the end bolster are pre-bent and partially insulated "tentacles" intended to contact the gastrointestinal mucosa. A plurality of electrodes is provided to ensure that, once the device is placed, at least one electrode is in contact with the mucosa.

U.S. Pat. No. 5,690,691, issued on November 25 to J. Chen et al., discloses a gastrointestinal pacemaker having phased multi-point stimulation. A portable or implantable gastric pacemaker includes multiple electrodes that are positionable on the inner or outer surface of an organ in the gastrointestinal tract, the multiple electrodes being positioned at multiple sites.

U.S. Pat. No. 6,542,776, issued on Apr. 1, 2003 to P. Gordon et al., discloses a gastric stimulator apparatus and a method for installing the apparatus. The apparatus comprises an implantable pulse generator, a lead system, and an electrode assembly or implant device. The apparatus is installed, preferably, through a trocar inserted through the patients skin. A series of trocars may be installed to allow for access of surgical instruments, as well as for a laparoscope to allow viewing of the attachment process.

U.S. Pat. No. 6,535,764, issued on Mar. 18, 2003 to M. Imran et al., discloses a gastric treatment device and method that includes an electronic stimulation device, which is attached to the interior of the stomach by an anchor device. The anchor device may have an electrode that contacts the stomach wall when the device is implanted through the stomach wall. A contact on the anchor device connects the electrode electrically to an electronic circuit within the stimulation device once the stimulation device is placed onto the anchor.

To the best of the inventor's knowledge, currently gastric electrodes are implanted by either laparascopic or open surgical techniques. There is a need for a device and method for placement of electrodes in the gastrointestinal tract by endoscopic techniques. This is because it is desirable, in any form of GES therapy, to minimize the surgically invasive nature of procedures used to implant electrodes, and to minimize risks associated with general anesthesia and surgical techniques including bleeding, infection, pain, and others.

None of the above inventions and patents, taken either singly or in combination, is seen to describe the instant invention as claimed. Thus, the device and method for placement of electrodes in the GI tract of the present invention solving the aforementioned problems is desired.

SUMMARY OF THE INVENTION

The device and method for placement of electrodes or other instruments in the GI tract allows for placement of electrodes for GES into the gastric wall using endoscopic techniques. Endoscopic placement of the electrodes provides for faster, easier, and safer placement than surgical placement. Additionally, endoscopic placement can be performed without the need for general anesthesia, using sedation and a local anesthetic instead.

The device for placement of electrodes in the GI tract is endoscopically placed. The device comprises one or more electrodes disposed on a housing. The housing is an elongated body having a pointed first end. A bolster is disposed on a second end of the body. When placed within the GI tract, the first end of the device extends through the gastric and abdominal walls, extending outside of the patient's body. The device is held in place by the bolster, which is in contact against the inner lining of the gastric wall.

The electrodes are exposed at the surface of the housing body, and contact the gastric smooth muscle when the device is in position. Insulated wires in electrical connection with the electrodes extend the length of the housing body. Once the device is placed, the first end of the housing body and the wire insulation are stripped away to expose the wires, allowing electrical connection to an external electrical signal generator to provide electrical stimulus.

A small wire or cord placement loop is attached to the first end of the housing body to facilitate endoscopic placement of the device. The basic placement procedure involves inserting a hollow needle into the patient's abdomen, through the abdominal wall and through the gastric wall at the site where the electrodes are to be placed. A guide wire is inserted into the GI tract through the needle, and withdrawn through the patient's mouth with the aid of an endoscope. The device's placement loop is attached to the guide wire, and the guide wire is then withdrawn, pulling the device through the patient's mouth and esophagus into the stomach and placed against the gastric wall with the first end of the device's body extending through the abdominal wall. Once placed, the device's wires are exposed and connected to a source of electrical stimulation. The source of electrical stimulation may be an external pacemaker or an implanted gastric pacemaker.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
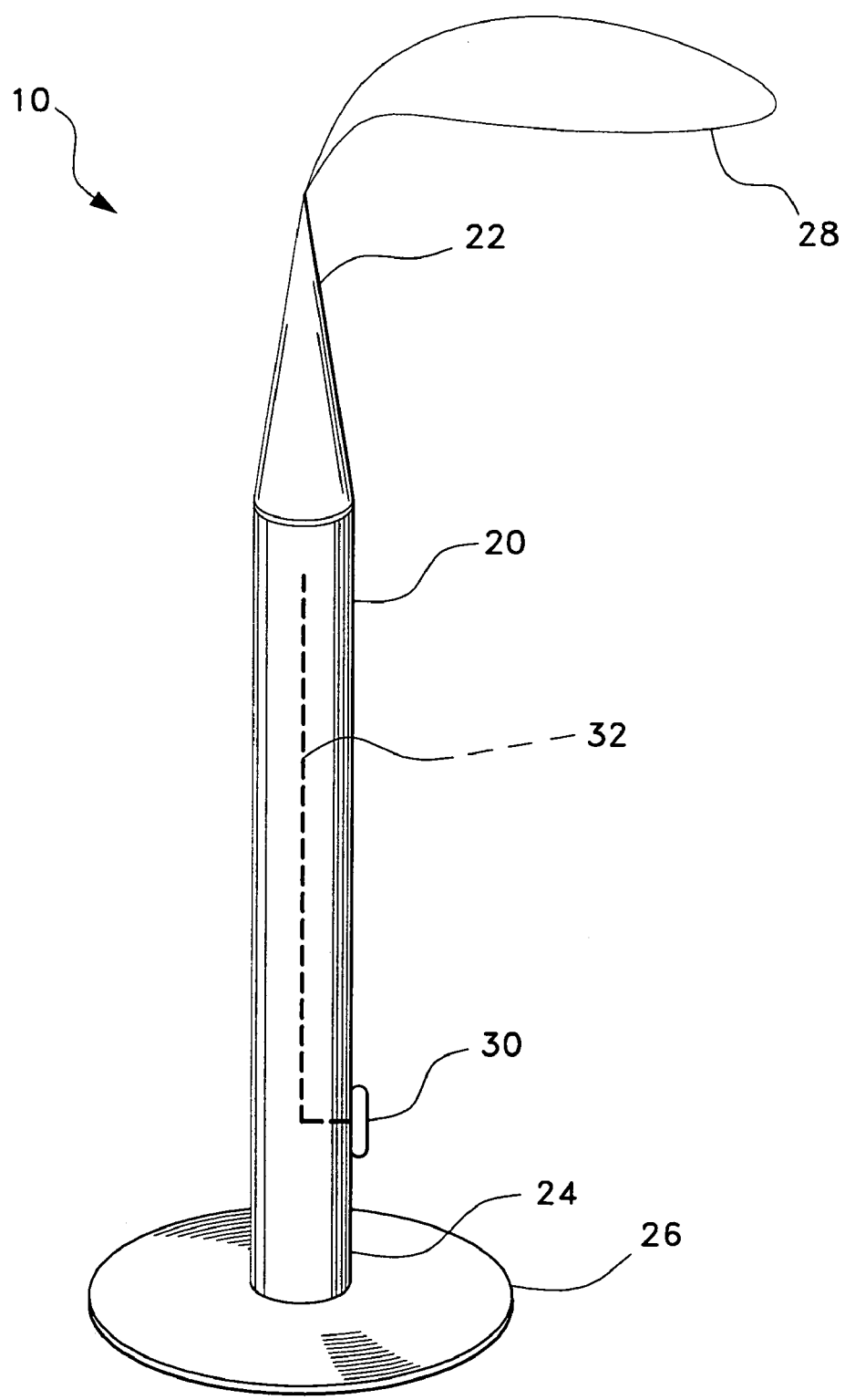
FIG. 1 is a perspective view of a device for placement of electrodes in the GI tract according to the present invention.

The present invention is a device and method for placement of electrodes in the GI tract. The device, designated generally as 10 in the drawings, allows electrode placement for gastric electrical stimulation (GES) using a minimally invasive endoscopic technique.

Figure 2:
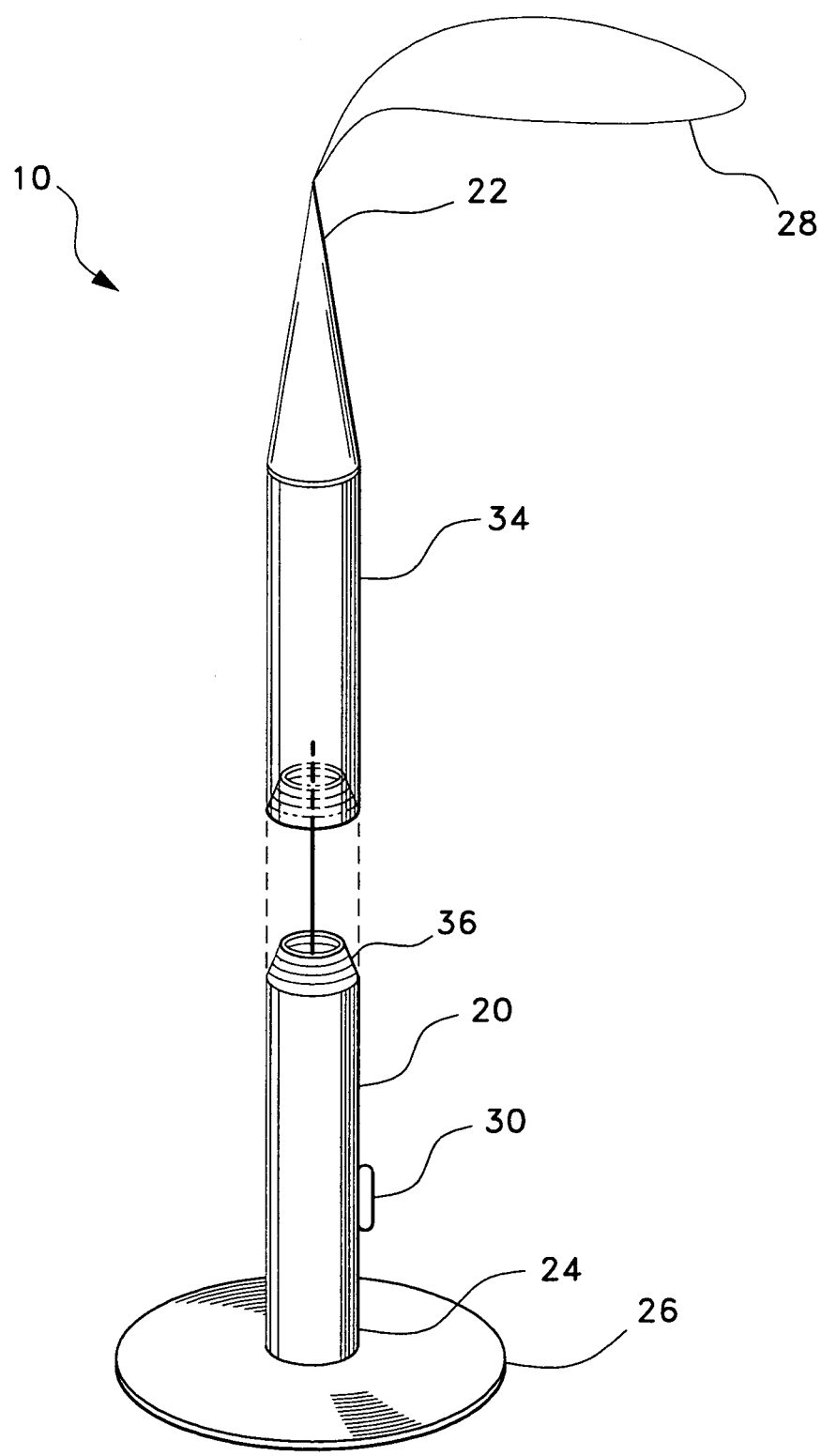
FIG. 2 is a perspective view of an embodiment of a device for placement of electrodes in the GI tract of the present invention having a removable portion to expose wires contained within.

Referring to FIGS. 1 and 2, the device 10 for placement of electrodes in the GI tract comprises an elongated body 20 having a first end 22 that is tapered to a point, and a second end 24, there being a first retaining member, such as a retainer disk or bolster 26, disposed on the second end 24. The device 10 carries at least one electrode 30, which may be disposed along the length of the elongated body 20. A wire 32 in electrical connection with the electrode 30 is contained within the body 20, and runs lengthwise generally toward the first end 22 of the device 10. The wire 32 is preferably insulated and sterile. Additional wired electrodes may be disposed on the device 10. Once the device 10 is placed, a portion 34 of the body 20 is removed to expose the electrode wire(s) 32 contained within. The removable first end portion 34 of the body 20 may be removably coupled to the body 20 with a threaded junction 36 similar to a leur lock, or by a frangible region of the body 20 whereby the removable portion 34 will break away from the body 20 relatively easily. A wire or cord placement loop 28 is attached to the first end 22 of the body 20 to allow attachment of the device 10 to a guide wire during the placement procedure.

The device 10 is intended for endoscopic placement into the GI tract, bringing the electrode 30 into contact with the gastric smooth muscle where electrical stimulation is desired. Placement of the device 10 follows a generally conventional percutaneous endoscopic gastrostomy (PEG) technique known as the "pull" method. Following known procedures of gastric insufflation to bring the stomach into apposition with the abdominal wall, and endoscopic translumination of the abdominal wall to identify the implant site, a hollow needle is inserted through the abdominal wall and into the gastric lumen. A guide wire is inserted through the needle and into the gastric lumen, from whence the guide wire is withdrawn through the patient's mouth. The device 10 is attached to the guide wire using the placement loop 28, and the device 10 is drawn through the patient's mouth and esophagus into the stomach and is positioned by the guide wire.

Figure 3:
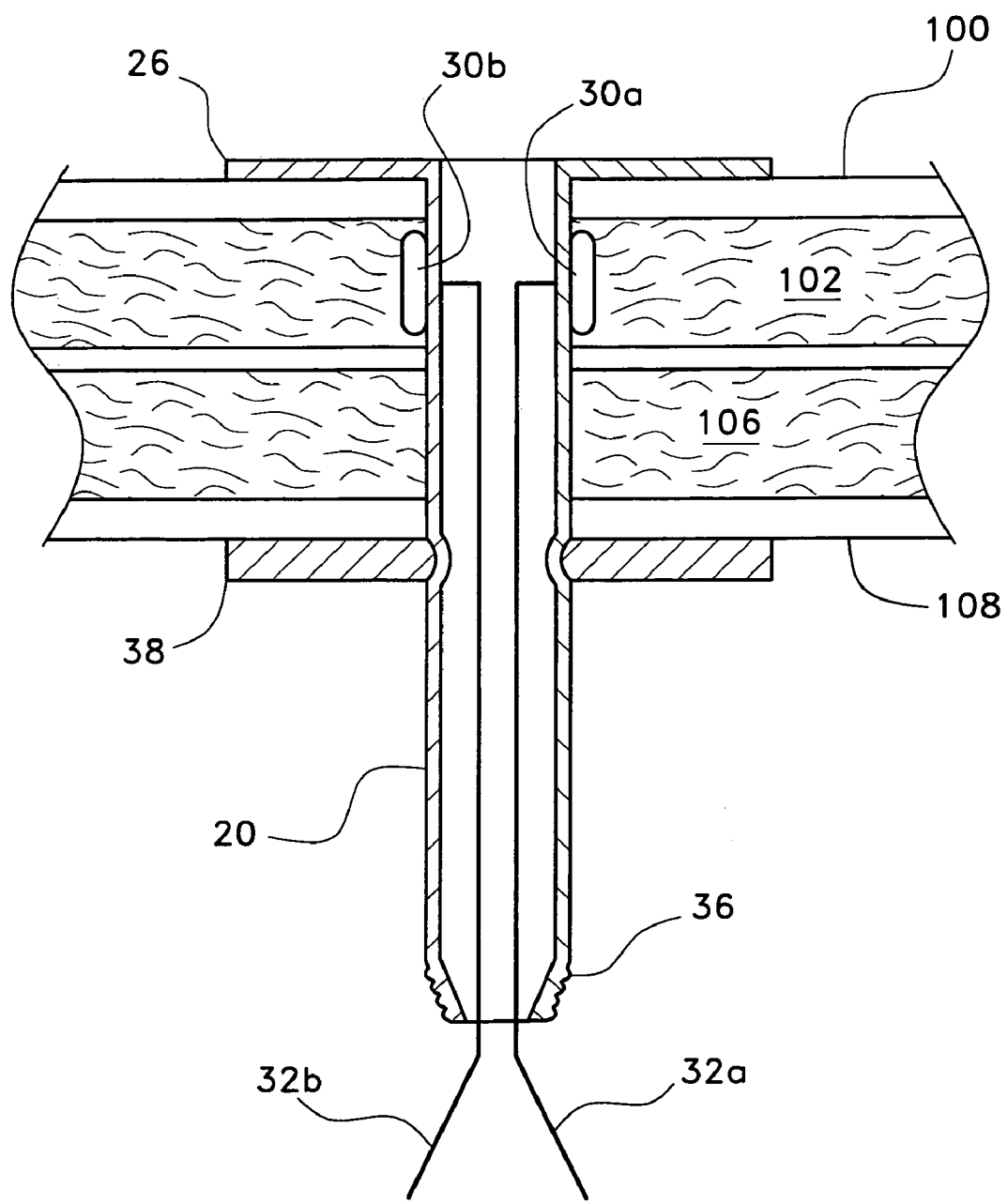
FIG. 3 is an environmental section view of a device for placement of electrodes in the GI tract of the present invention placed within the GI tract.

Turning to FIG. 3, an embodiment of the device 10 having two electrodes 30a, 30b, each separately wired by wires 32a, 32b, is shown placed in the patient's body. The bolster 26 is in contact with the gastric wall 100, and the electrodes 30a, 30b are in contact with the gastric smooth muscle 102. The elongated body 20 of the device 10 extends through the gastric wall 100, muscle tissue 102, the abdominal wall 106, and the outer skin 108, delivering the wires 32a, 32b to the exterior of the patient's body. A retaining member 38 is placed over the body 20 of the device 10 to secure the device 10 in place. Once placed, the end portion 34 is removed to expose the wires 32a, 32b. The wires 32a, 32b may then be connected to an electrical signal generator, such as a gastric pacemaker. It can be noted that the pacemaker may be an external pacemaker or an implantable device.

Figure 4A:
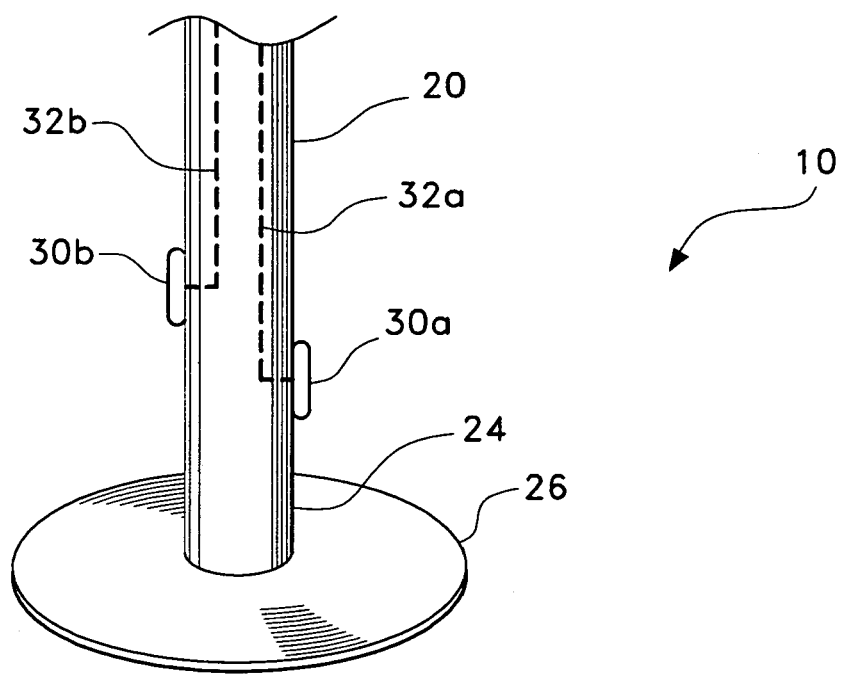
FIG. 4A is a partial perspective view of a device for placement of electrodes in the GI tract of the present invention having two electrodes.
Figure 4B:
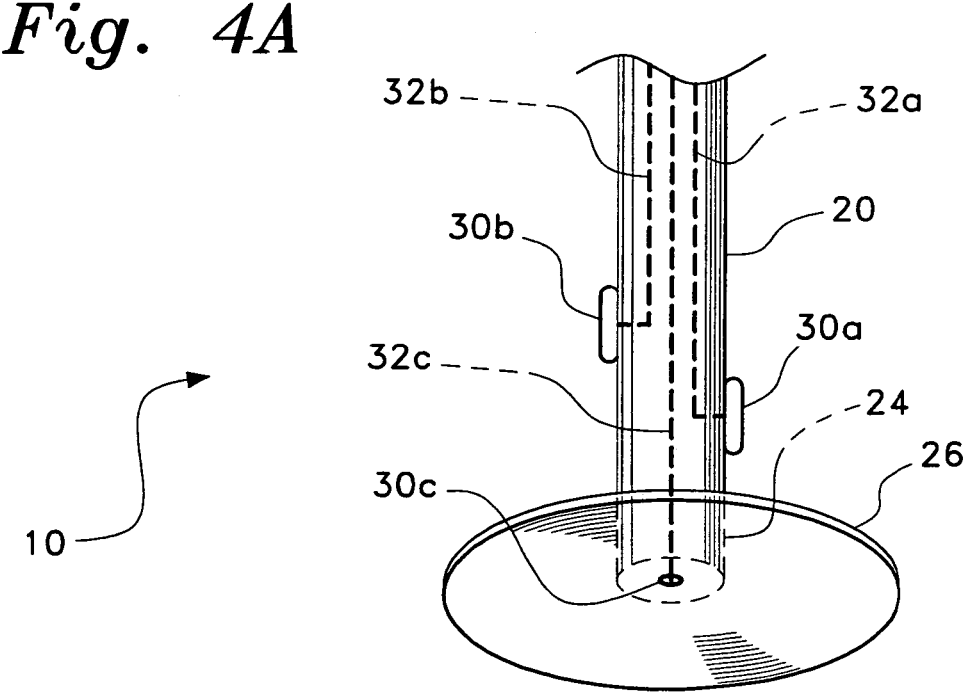
FIG. 4B is a partial perspective view of a device for placement of electrodes in the GI tract of the present invention having three electrodes.
Figure 5:
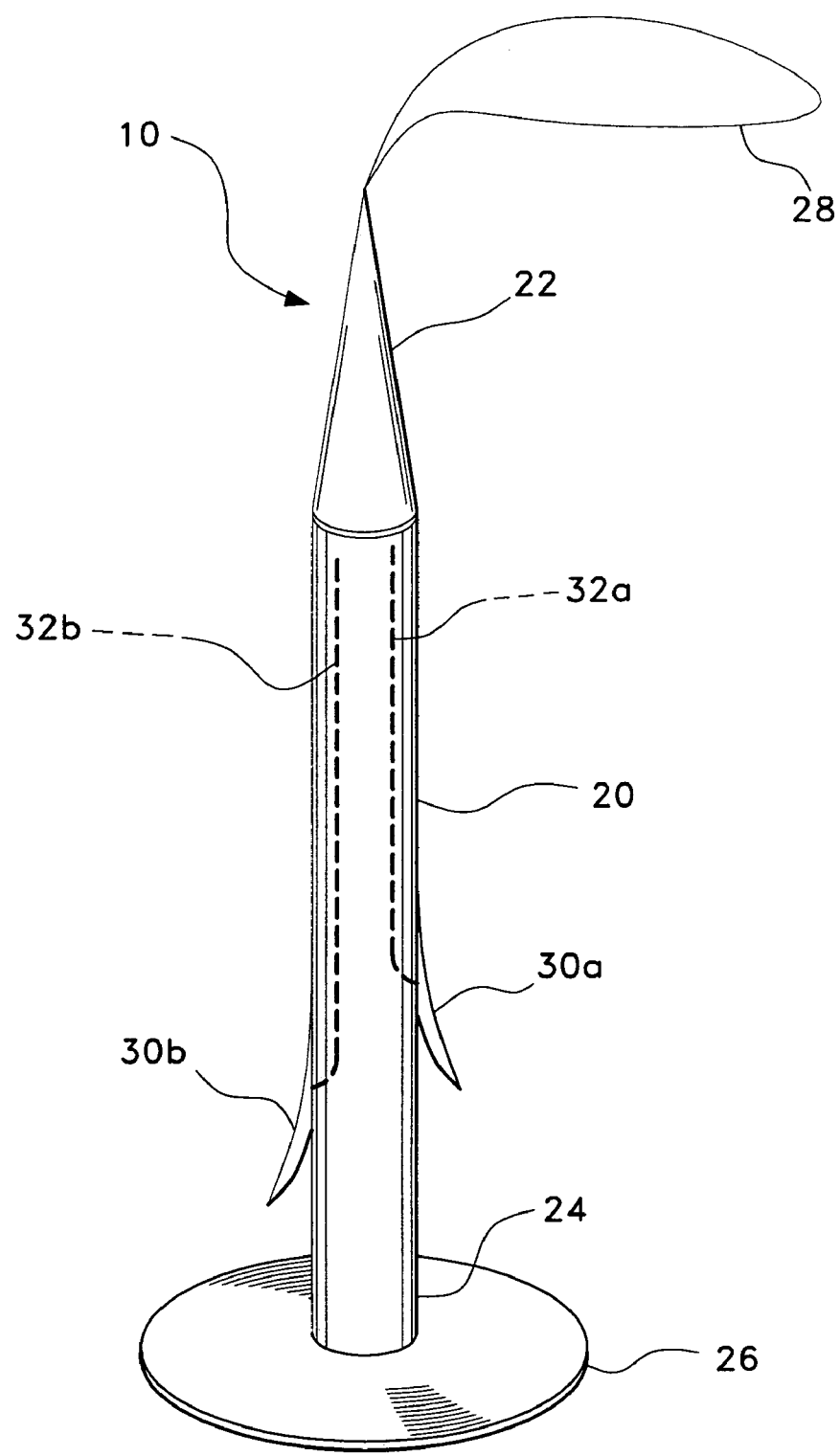
FIG. 5 is a perspective view of a device for placement of electrodes in the GI tract of the present invention having barbed electrodes.

Turning now to FIGS. 4A, 4B, and 5, alternative embodiments of the device 10 are shown having differing electrode arrangements. FIG. 4A shows a device 10 having two electrodes 30a and 30b disposed along the body 20 of the device 10 in electrical communication with wires 32a and 32b, respectively. In FIG. 4B a device 10 is shown similar to the device 10 seen in FIG. 4A, but with an additional electrode 30c disposed on the luminal surface of the bolster 26, the electrode 30c being in electrical communication with wire 32c. Such an electrode 30c is useful for measuring osmolality within the gastric lumen. In FIG. 5, electrodes 30a and 30b are barbed to increase retention of the device 10 in position and to increase electrical contact with the gastric smooth muscle.

Although the above specification and drawings describe a device and method for the placement of electrodes in the gastrointestinal tract by endoscopic techniques, one skilled in the art will recognize that the device and method may be used to implant other instruments, such as a camera and light mechanism, a recorder of gastric motility, a recorder of eating patterns, a pH monitor, an osmolality monitor, an oxygen saturation monitor, a blood flow monitor, and any other similar instruments.

It is to be understood that the present invention is not limited to the embodiments described above, but encompasses any and all embodiments within the scope of the following claims.

I claim:

1. A device for placement of electrodes in a GI tract, comprising:
    an elongated body having a first end and a second end, the first end being pointed, the elongated body having a removable first end portion;
    a first retaining member disposed on the second end of said elongated body; and
    at least one electrode disposed along said elongated body, the electrode having a wire extending within and toward the first end of said elongated body;
    whereby the device is adapted for being drawn into the GI tract by endoscopic techniques so that the pointed first end extends from a patient's abdomen, the first retaining member being lodged against the patient's stomach wall.

2. The device for placement of electrodes according to claim 1, further comprising a placement loop attached to the first end of said elongated body.

3. The device for placement of electrodes according to claim 1, further comprising a second retaining member, the second retaining member being placed over the elongated body of the device once the device is placed in the GI tract.

4. The device for placement of electrodes according to claim 1, wherein said at least one electrode comprises a retaining member electrode attached to a luminal surface of the first retaining member.

5. The device for placement of electrodes according to claim 1, wherein the at least one electrode is barbed.

6. A method for placing the device of claim 1 in the GI tract of a patient's body, comprising the steps of:
    inserting a guide wire through the patient's abdominal wall and into the gastric lumen;
    withdrawing said guide wire from the patient's mouth;
    affixing said device to said guide wire;
    using said guide wire to draw said device into position against the gastric wall; and
    removing the removable first end portion of said device to expose the wires.

7. The method for placing the device according to claim 6, further comprising the step of placing a second retaining member over the body of the device, subsequent to drawing said device into position against the gastric wall.

8. The method for placing the device according to claim 6, further comprising the step of connecting the wires to an electrical signal generator.

9. The method for placing the device according to claim 6, further comprising the step of attaching the guide wire to a placement loop attached to the first end of said elongated body.

10. The method for placing the device according to claim 6, wherein the removable first end portion of the device is removably coupled to the device with a threaded junction.

11. A device for placement of an instrument in a GI tract, comprising:
    an elongated body having a first end and a second end, the elongated body having a removable first end portion, the first end being adapted for being drawn through a needle puncture in a patient's abdominal wall;
    a first retaining member disposed on the second end of said elongated body; and
    at least one instrument disposed at least partially within said elongated body;
    whereby the device is adapted for being drawn into the GI tract by endoscopic techniques so that the first end extends from a patient's abdomen, the first retaining member being lodged against the patient's stomach wall, the instrument being accessible by removal of the first end portion.

12. The device for placement of instrument according to claim 11, further comprising a placement loop attached to the first end of said elongated body, the placement loop being adapted for attachment of a guide wire.

13. The device for placement of instrument according to claim 11, further comprising a second retaining member, the second retaining member being placed over the elongated body of the device once the device is placed in the GI tract.

14. The device for placement of instrument according to claim 11, further comprising:
    a retaining member electrode attached to a luminal surface of the first retaining member; and
    a wire extending within and toward the first end of said elongated body.

15. The device for placement of instrument according to claim 11, wherein said instrument comprises an electrode having a contact surface extending to an exterior of the elongated body adjacent the first retainer and a wire extending through the elongated body into the removable end portion, the wire being adapted for connection to a voltage source.

16. A method for placing the device of claim 11 in the GI tract of a patient's body, comprising the steps of:
    inserting a guide wire through the patient's abdominal wall and into the gastric lumen;
    withdrawing said guide wire from the patient's mouth;
    affixing said device to said guide wire;
    using said guide wire to draw said device into position against the gastric wall; and
    removing the removable first end portion of said device in order to access the instrument.

17. The method for placing the device according to claim 16, further comprising the step of placing a second retaining member over the body of the device, subsequent to drawing said device into position against the gastric wall.

18. The method for placing the device according to claim 16, wherein the instrument comprises at least one electrode having a lead wire, further comprising the step of connecting the lead wire to an electrical signal generator.

19. A device for placement of an instrument in a GI tract, comprising:
    an elongated hollow body having a first end and a second end, the elongated body having a removable first end portion, the first end being adapted for being drawn through a needle puncture in a patient's abdominal wall, the elongated hollow body being adapted for receiving at least a portion of an instrument therein; and
    a first retaining member disposed on the second end of said elongated body;
    whereby the device is adapted for being drawn into the GI tract by endoscopic techniques so that the first end extends from a patient's abdomen, the first retaining member being lodged against the patient's stomach wall, the instrument being accessible by removal of the first end portion.

20. A method for placing the device of claim 19 in the GI tract of a patient's body, comprising the steps of:
    inserting a guide wire through the patient's abdominal wall and into the gastric lumen;
    withdrawing said guide wire from the patient's mouth;
    affixing said device to said guide wire;
    using said guide wire to draw said device into position against the gastric wall; and
    removing the removable first end portion of said device.

* * * * *